(12) United States Patent
Demarest et al.

(10) Patent No.: US 8,746,505 B2
(45) Date of Patent: Jun. 10, 2014

(54) MULTI-SENSORY PRODUCT COMBINING REEDS, VOLATILE ACTIVES DIFFUSION, FORM-WITHIN-A-FORM CONSTRUCTION, AND LIGHT SHOW CAPABILITIES

(75) Inventors: Scott W. Demarest, Caledonia, WI (US); Simon M. Conway, Burlington, WI (US); Kevin Harrity, Oak Creek, WI (US); Scott D. Walter, Twin Lakes, WI (US); David R. Carlson, Cedarburg, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1077 days.

(21) Appl. No.: 12/734,276

(22) PCT Filed: Oct. 29, 2008

(86) PCT No.: PCT/US2008/081593
§ 371 (c)(1), (2), (4) Date: Feb. 17, 2011

(87) PCT Pub. No.: WO2009/058872
PCT Pub. Date: May 7, 2009

(65) Prior Publication Data
US 2011/0148329 A1    Jun. 23, 2011

Related U.S. Application Data

(60) Provisional application No. 60/983,375, filed on Oct. 29, 2007.

(51) Int. Cl.
*B65D 5/66*    (2006.01)

(52) U.S. Cl.
USPC ........ 222/113; 222/146.1; 239/128; 422/122; 362/96

(58) Field of Classification Search
USPC ........ 222/113, 144, 146.1, 146.2, 146.6, 639, 222/644; 422/120, 122; 362/85, 96, 362, 362/373; 239/128, 135, 302
See application file for complete search history.

(56) References Cited

U.S. PATENT DOCUMENTS

| | | | |
|---|---|---|---|
| 3,747,902 A | 7/1973 | Bailey |
| 3,804,331 A | 4/1974 | Levey |
| 4,020,978 A | 5/1977 | Szczepanski |
| 4,327,518 A | 5/1982 | Knauff |
| 4,377,399 A | 3/1983 | Bryson |
| 4,452,393 A | 6/1984 | Schimanski et al. |
| 4,666,638 A | 5/1987 | Baker et al. |
| 4,743,406 A | 5/1988 | Steiner et al. |
| 4,931,224 A | 6/1990 | Holzner, Sr. |
| 5,050,798 A | 9/1991 | Sullivan |
| 5,269,460 A | 12/1993 | Hautmann |

(Continued)

*Primary Examiner* — Thuy Vinh Tran (57) ABSTRACT

A multi-sensory product able to disperse chemical actives using reeds or other wicks, as well as providing a light show is disclosed. The product includes a form-within-a-form design wherein the inner form or vase is able to store the chemical actives, as well as mount the reeds or other wicks. The outer vase complements the aesthetics of the inner vase while at the same time concealing the electronics of the device. The electronics of the device can include a power source, as well as a circuit board for driving LEDs mounted thereon. The LEDs can generate a light show which can be refracted and diffused through the glass or polymer material forming the inner and outer vases thereby creating an aesthetically pleasing and multi-sensory experience through the use of the product.

16 Claims, 10 Drawing Sheets

(56) References Cited

U.S. PATENT DOCUMENTS

| | | |
|---|---|---|
| 5,353,546 A | 10/1994 | Bock |
| 5,526,830 A | 6/1996 | Hunter |
| 5,547,616 A | 8/1996 | Dancs et al. |
| 5,573,325 A | 11/1996 | Lekowski |
| 5,891,400 A | 4/1999 | Ansari et al. |
| 6,406,673 B1 | 6/2002 | Soller et al. |
| 6,513,725 B1 | 2/2003 | Slade |
| 6,663,838 B1* | 12/2003 | Soller et al. ............... 422/125 |
| 6,912,355 B2 | 6/2005 | Vieira |
| 7,350,720 B2* | 4/2008 | Jaworski et al. ............. 239/55 |
| 7,824,627 B2* | 11/2010 | Michaels et al. ............ 422/128 |
| 2001/0012495 A1 | 8/2001 | Furner et al. |
| 2005/0084569 A1 | 4/2005 | Hu et al. |
| 2005/0169666 A1 | 8/2005 | Porchia et al. |
| 2005/0169812 A1 | 8/2005 | Helf et al. |
| 2005/0249474 A1 | 11/2005 | Tan |
| 2006/0002102 A1 | 1/2006 | Leonard |
| 2006/0081721 A1 | 4/2006 | Caserta et al. |
| 2006/0120080 A1* | 6/2006 | Sipinski et al. ............. 362/253 |
| 2006/0152946 A1 | 7/2006 | Chien |
| 2006/0263733 A1 | 11/2006 | Furner et al. |
| 2007/0086199 A1 | 4/2007 | Demarest et al. |
| 2007/0133206 A1 | 6/2007 | Demarest et al. |
| 2007/0185434 A1 | 8/2007 | Denisart et al. |
| 2008/0298046 A1* | 12/2008 | Samuel et al. ............... 362/96 |

\* cited by examiner

MULTI-SENSORY PRODUCT COMBINING REEDS, VOLATILE ACTIVES DIFFUSION, FORM-WITHIN-A-FORM CONSTRUCTION, AND LIGHT SHOW CAPABILITIES

CROSS-REFERENCE TO RELATED APPLICATION

This application is an international application which is based on and claims priority under PCT Rule 4.10(a) from provisional Application Ser. No. 60/983,375, filed on Oct. 29, 2007 in the United States of America.

FIELD OF THE DISCLOSURE

The present disclosure generally relates to fragrance and other volatile actives dispensers, as well as light sources, and more particularly relates to devices capable of performing both functions.

BACKGROUND OF THE DISCLOSURE

Dispensers for volatile actives can be provided in a variety of forms. They can be as simple as scented candles which when lit melt the underlying wax. Since the wax has already been impregnated with a fragrance, this heating and melting of the wax disperses the fragrance into the air. With other devices, the heating source may be provided by way of an electrical outlet. For example, the Glade® Plug-In® devices offered by the assignee of the present disclosure can be mounted into a conventional electrical outlet and be provided with a heating source powered thereby. A package or cartridge of fragranced oil can be positioned proximate the heating source such that when activated, the gel is heated and the fragrance is dispersed. Such diffusers can be augmented by the inclusion of an electric fan which increases the ability of the fragrance to be dispersed into the ambient air.

In still further devices, the active need not be provided simply in the form of a fragrance, but can be provided in the form of an insecticide, deodorizer, or the like. Such active substances can also be proactively dispersed by the user. Rather than having the device simply plugged into an electrical outlet which continually disperses the active, the diffuser can be user activated wherein the user physically depresses or rotates some portion of a housing to cause the fragrance or active to be dispersed. In still others, a timer or counter can be electrically incorporated into the device so as to disperse the active in regular intervals. Such a device is marketed by the present assignee, under its Wisp® brand.

In still further devices, wicks can be used to draw the fragranced oil from a reservoir at a controlled pace. The active can then be dispensed simply by exposure to the ambient environment, or a fan or the like can be positioned proximate the wick so as to increase the ability of the active to be so dispensed. Such wicks can be fabric based but any number of different devices can be used which employ capillary action to draw the fragranced oil up from the reservoir.

One example of the wicks is provided in the form of reeds. Reeds are a natural plant substance with two examples being rattan and wicker. The use of such substances is not only effective, but environmentally sound. With such devices, the supply of fragranced active is provided in a vessel or a vase with the reeds being upstanding within the vase to wick the substance therethrough and simply by exposure to the ambient air dissipate the active into the surrounding air.

While such devices are effective and have been met with substantial commercial success, there continues to exist a need for such devices which improve upon existing aesthetics, their ability to dispense the active, and overall sensory impact. For example, lights and colored light show sources currently exist but have not heretofore been effectively incorporated with a reed diffuser.

SUMMARY OF THE DISCLOSURE

In accordance with one aspect of the disclosure, a multi-sensory dispenser is disclosed which comprises inner and outer forms. At a bottom portion of one of the inner and outer forms is provided a light source to project light on and/or through the inner and outer forms. At least one of the inner and outer forms contains a volatile active. The multi-sensory dispenser may also include at least one reed having a bottom end inserted into the inner and/or outer form to be in contact with the volatile active.

In one embodiment, the multi-sensory dispenser may include an outer form defining an interior space, and an inner form having an open top disposed outside of the interior space of the outer form and a closed bottom disposed within the interior space of the outer form. The dispenser further includes a volatile active disposed in one of the inner and outer forms, and a light source disposed in a bottom portion of one of the inner and outer forms.

In another embodiment, the multi-sensory dispenser may include a base having a top recess, and an inner form having an open top and a closed bottom with a lock shaped to be matably received in the top recess of the base. The dispenser further includes a volatile active disposed in the inner form and a light source disposed in the base. The dispenser may also include an outer form upwardly extending from the base around the inner form.

In yet another embodiment of this disclosure, the multi-sensory dispenser may include an outer form, an inner form, a volatile active disposed in one of the inner and outer forms, and a light source disposed in a bottom portion of one of the inner and outer forms. The inner and outer forms define an air passageway therebetween. The dispenser further includes an air flow device disposed in or mounted on a bottom portion of one of the inner and outer forms to facilitate air flow through the air passageway.

In accordance with one aspect of the disclosure, a multi-sensory dispenser and light source is disclosed which comprises a base, an outer vase and an inner vase. The base houses at least one light source, a power source and electronics for controlling both. The outer vase upwardly extends from the base. The inner vase upwardly extends from the base as well within the outer vase. A volume of volatile active is provided in the inner vase. A plurality of reeds may be partially immerged in the volume of volatile active.

In accordance with another aspect of the disclosure, a multi-sensory dispenser and light source is disclosed which comprises a base, an outer vase, and an inner vase. The base houses at least one light source, a power source, and electronics for controlling the light source and power source. The outer vase and inner vase upwardly extend from the base, with the inner vase upwardly extending within the outer vase. The inner vase is mounted relative to the outer vase in a form-within-a-form manner so as to create an air space therebetween allowing air flow to pass over the inner vase within the outer vase thereby assisting with the dissipation of the active.

In accordance with yet another aspect of the disclosure, a multi-sensory dispenser and light source is disclosed which comprises a base housing at least one light source, a power source, and electronics for controlling the light source and power source. An outer vase and inner vase upwardly extend from the base with the inner vase upwardly extending within the outer vase. The inner vase includes a bottom surface shaped complementarily to an opening in the base. The electronics of the device may be activated by a sliding or rotational movement of the inner vase after the bottom surface of the inner vase is reciprocally received in the opening of the base.

These and other aspects and features of the disclosure will become more apparent upon reading the following detailed description when taken in conjunction with the accompanying drawings.

While the present disclosure is susceptible to various modifications and alternative constructions, certain illustrative embodiments thereof have been shown in the drawings will be described below in detail. It should be understood, however, that there is no intention to limit the disclosure to the specific forms disclosed, but on the contrary, the intention is to cover all modification, alternative constructions, and equivalents falling within the spirit and scope of the disclosure as defined by the appended claims.

DETAILED DESCRIPTION OF THE DISCLOSURE

Figure 1:
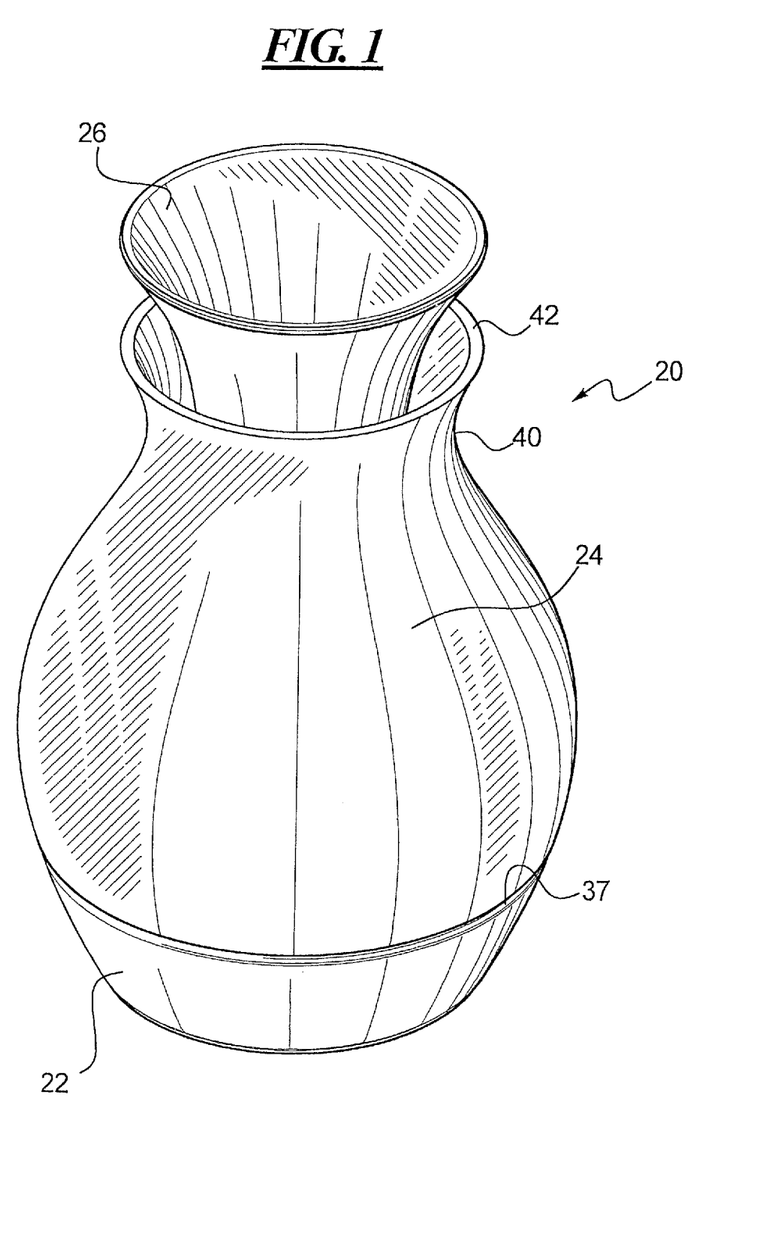
FIG. 1 is a isometric view of a volatile actives dispenser and light source constructed in accordance with the teachings of the disclosure.

Referring now to the drawings and with specific reference to FIG. 1, a multi-sensory dispenser constructed in accordance with the teachings of the disclosure is generally referred to as reference numeral 20. While the device 20 is shown to include specific shapes in the pending application, with FIGS. 1-8 depicting one embodiment and FIGS. 9-13 depicting another two, it is to be understood that the other exterior shapes are certainly possible and covered by the scope of this disclosure. The depicted shapes are merely exemplary. Moreover, the device will be described as having inner and outer vases. The term "vases" as used herein is broadly defined as any form, shape or housing and need not be contoured as shown.

Referring again to FIG. 1, the device 20 is shown to include a base 22 from which upwardly extends an outer vase 24, as well as an inner vase 26. The base in the depicted embodiment is substantially circular in horizontal cross-section. Mounted within the base in the depicted embodiment is an electronics assembly 28 (see FIG. 2). However, it is to be understood that a distinct "base" for the electronics need not be provided. Rather the light source, power source and optional electronics assembly may be placed directly within one of the inner and outer vases.

Starting with the base 22, it is shown to include a circular bottom wall 30 upon which the base 22 and device 20 can sit in a stable fashion. A side wall 32 upwardly and outwardly extends from the circular bottom wall 30 and terminates in an upper rim 34. As shown best in the longitudinal sectional view of FIG. 2, the upper rim 34 is substantially circular, thereby creating a base 22 in the substantial shape of a bowl or the like.

Figure 2:
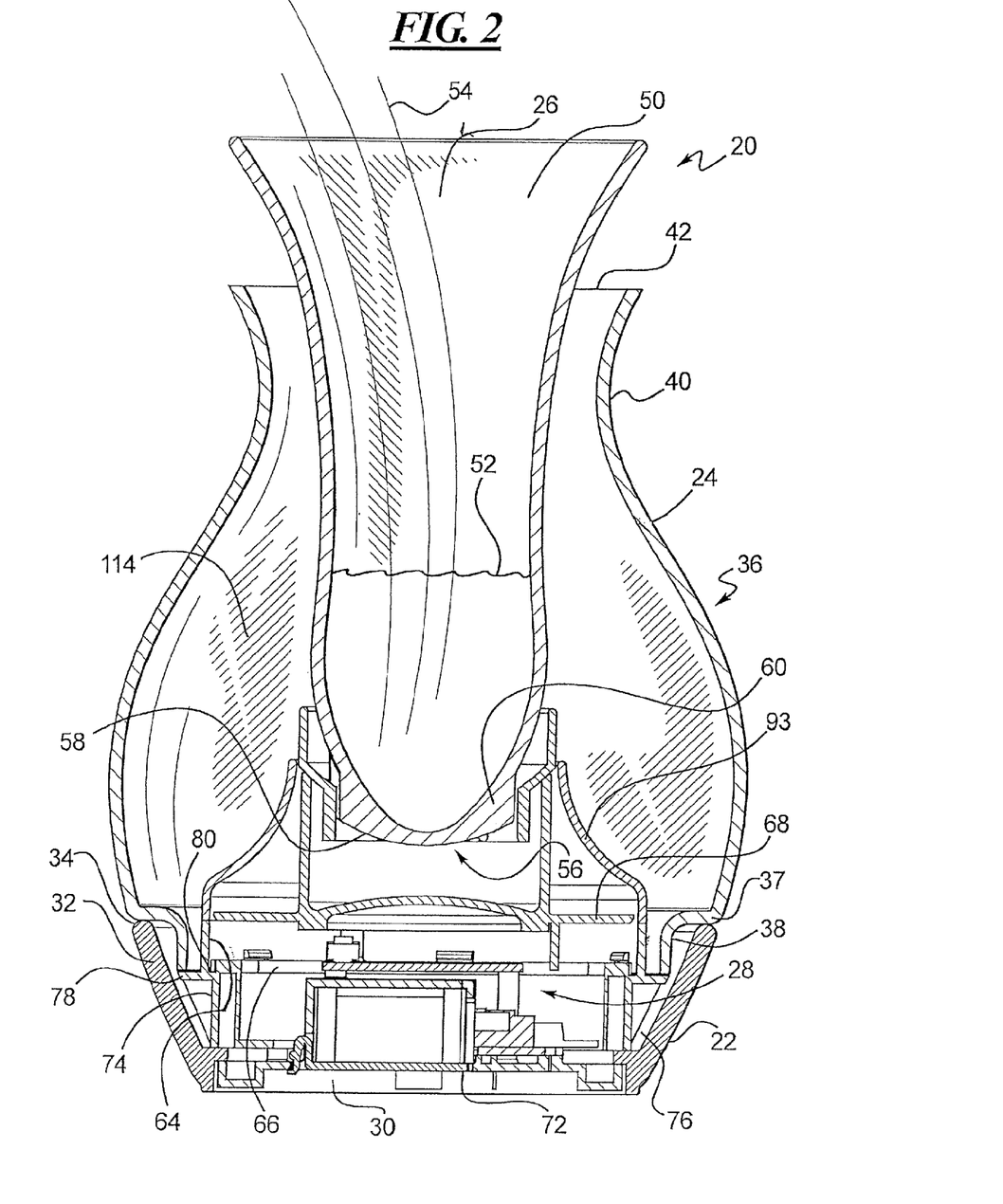
FIG. 2 is a side elevation view, in cross-section, of the device of FIG. 1.

Turning now to the outer vase 24, it is shown in FIG. 2 to include a bulbous side wall 36 having a circular bottom arm 37 matching the diameter of the base upper rim 34 which then tapers inwardly into a downwardly extending neck 38 so as to mate with the base 22. In the upward direction, the outer vase 24 extends radially outward from the bottom rim 37 in a bulbous fashion which then tapers back radially inward into a constricted neck 40. The constricted neck 40 then flares outwardly into an open mouth 42. Although the base 22 is shown to be detachable from the outer vase 24, it may also be constructed as an integral part of the outer vase or form 24.

Figures 3, 4:
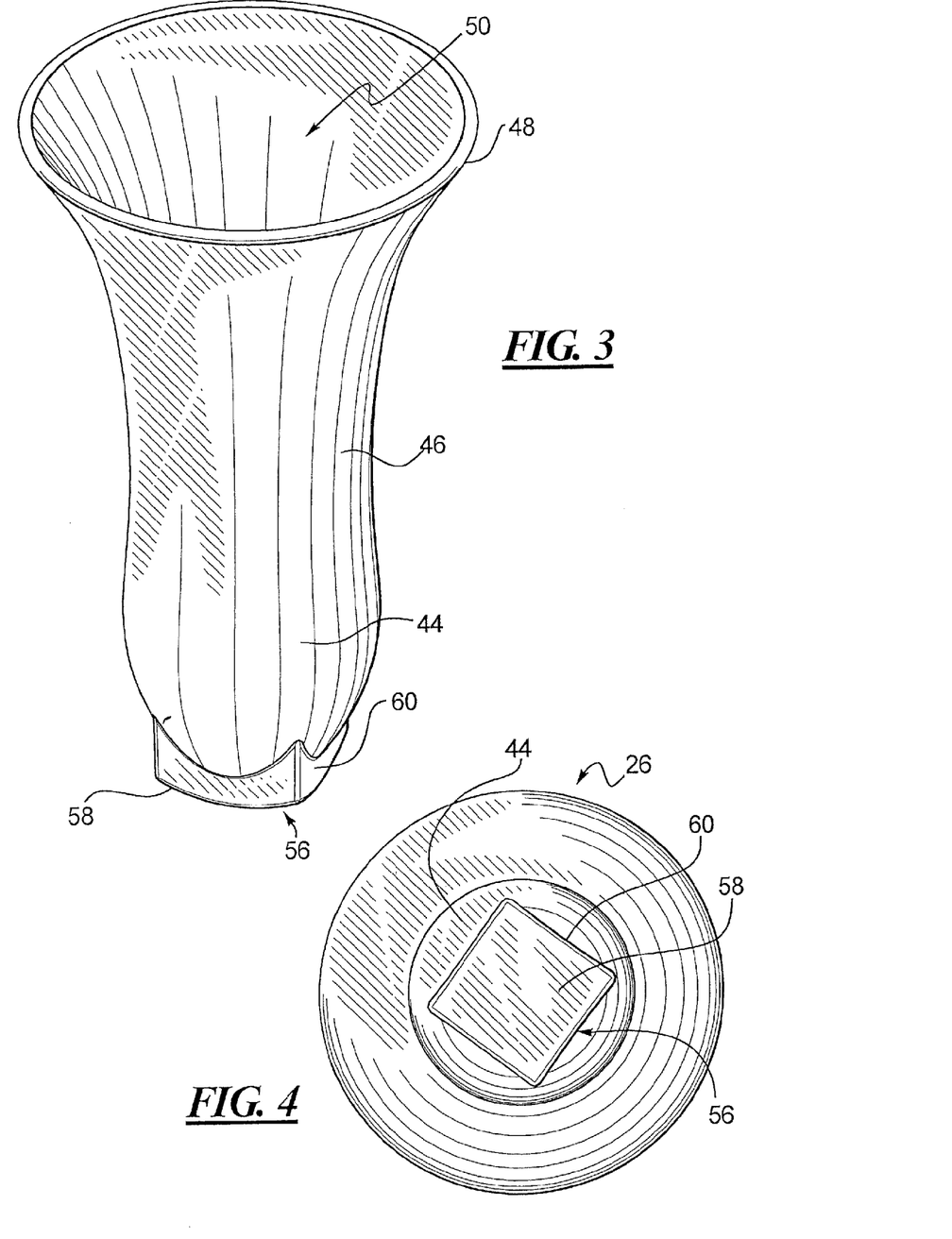
FIG. 3 is a perspective view of the inner vase of the device.
FIG. 4 is a bottom view of the inner vase.
Figure 5:
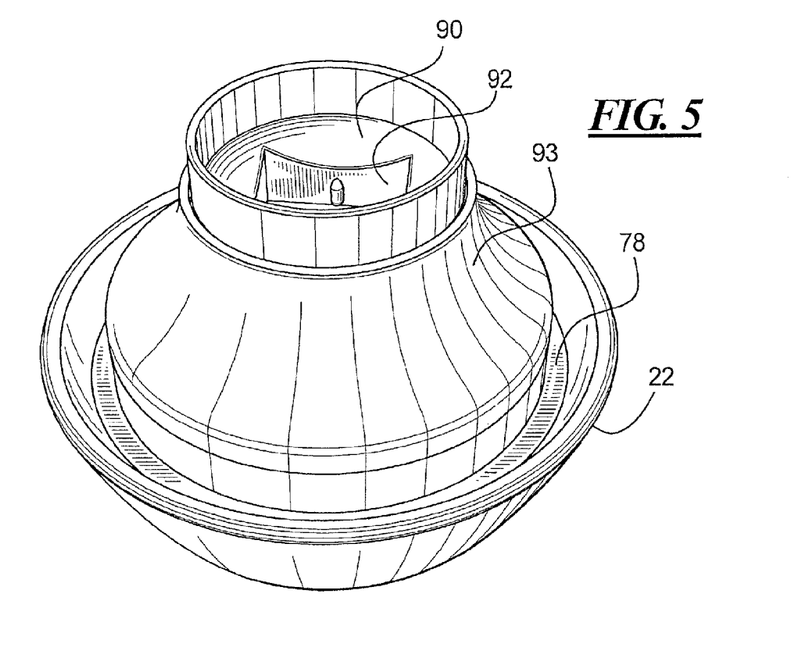
FIG. 5 is an isometric view of the base of the device.
Figure 6:
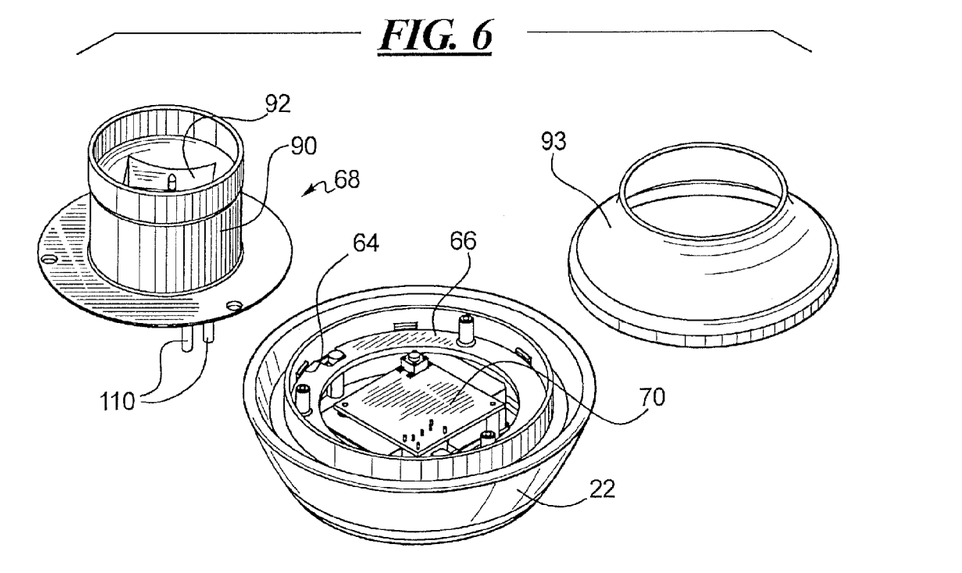
FIG. 6 is an isometric view of the base with the glamour plate and top diffuser exploded away.

With respect to the inner vase 26, as shown best in FIG. 3, it includes a closed end 44 from which upwardly extends a side wall 46, and an open top 48. The closed end 44 is substantially hemispherical in shape. The side wall 46 is substantially cylindrical in shape as it extends from the closed end, but then flares outwardly into the open top 48. In so doing, it can be seen that the inner vase 26 provides a storage space 50 for receipt of a fragranced oil 52 or the like. The fragranced oil 52 can be dissipated into the ambient air to freshen the air. Alternatively, other chemical actives such as an insecticide or the like can be provided therein for dissipation in a similar capacity. Upon depletion, the active may be refilled either by pouring from another container or by replacing the empty inner form with another inner form preloaded with the active.

In addition, as will be described in further detail herein, a plurality of reeds 54 can be provided in the inner vase 26 to wick the active 52 up and thereby facilitate the dissipation process as well. The reed suitable for use in the disclosed dispenser may be traditional reeds, dried natural plant materials with capillary actions, self-supportive wick materials, wick materials wrapped or sleeved around supporting structure (e.g. braided cotton around wire or woven cotton around wire), elongated ceramic or polymeric wick, and the like. Moreover, as opposed to an open volume of volatile active poured into the inner vase, the active can be provided in a cartridge with a removable or penetrable membrane. The volatile active may also be pre-impregnated into the reeds themselves.

The inner vase 26 may extend beyond the open mouth 42 of the outer vase 24 so that the open top 48 of the inner vase 26 is disposed outside of the interior space defined by the outer vase 24. Without wishing to be bound by any particular theory, it is contemplated that this configuration facilitates the interaction between the volatile active and the air flow around the dispenser, thereby improving the dispensing performance of the dispenser.

As illustrated in FIGS. 1-10, the inner vase 26 may be constructed as a one-piece open-top container that can be refilled by directly pouring the volatile active through the open top 48 into the inner vase 26. However, as illustrated in the alternative embodiment in FIGS. 11-12, the inner vase 306 may also be constructed as an assembly that includes, among other things, a replaceable reservoir 310. In this embodiment, the inner vase 306 includes a reservoir 310 having a threaded neck 311, an annular collar 308 threaded onto the neck 311 of the reservoir 310. The annular collar 308 has a center opening 313 in registry with the opening of the reservoir 310. The annular collar 308 also includes an annular groove 314 on its top surface to receive and secure the bottom of a shroud 307. In this embodiment, the shroud 307, collar 308, and reservoir 310 collectively form an inner vase 306 that can also be used separately as a stand-alone dispenser.

As will be noted in many of the views, particularly FIGS. 2-4, extending away from the closed end 44 of the inner vase 26 is a lock 56. In the depicted embodiment, the lock 56 is substantially square in horizontal cross-section, but in other embodiments different shapes including, but not limited to, trilobes, triangles, stars, polygons, ovals, etc., are possible. As shown best in FIG. 4, the lock 56 includes a curved bottom wall 58 and four side walls 60. Each of the side walls 60 extend transversely away from the hemispherical closed end 44. The side walls 60 then terminate in a curved bottom surface 58. The lock 56, as will be described in further detail herein provides an important interface function with the rest of the device 20. Although the bottom of the inner vase 26 in shown to have a curved surface in FIGS. 2-4, the lock 56 and the bottom of the inner vase 26 may take other forms, such as a lock with a flat bottom surface, that allows the inner vase 26 to be a stand-alone unit that is separated from the outer vase 24 and base 22.

With respect to material from which these components can be manufactured, it is envisioned that the base 22 will be manufactured from a ceramic material but other materials such as, but not limited to, glass and polymers are possible. As the base 22 houses the electronics assembly 28, it is advantageous for the base 22 to be substantially opaque, however.

With respect to the outer vase 24 and inner vase 26, they are envisioned to be glass but other materials such as, but not limited to, polymers and ceramics are possible as well. The glass can be provided in a transparent, translucent, frosted, colored, or opaque fashion. In addition, individual sections of those components can be provided in translucent, transparent, frosted, colored, or opaque capacities. In certain embodiments, it may be advantageous to provide only one of the inner and outer vases out of glass so as to minimize the likelihood of either breaking when removing or mounting them in the base. One or more of the inner and outer vases may also be etched, or provided with colored substrates or graphics to augment light refraction and aesthetic appeal. Moreover, one or more of the base, inner vase and outer vase may include a decorative inner and/or outer surface for enhanced light diffusion and aesthetics. The decorative surface may be smooth, textured, frosted, or combinations thereof. The frosted decorative surface may be manufactured by known methods, such as by spray coating or acid etching.

With respect to the electronics assembly 28, as shown in FIGS. 5-8, as well as the sectional view of FIG. 2, it may include an outer carriage 64, a lower support platform 66, an upper support platform 68, a circuit board 70, and a battery assembly 72. Starting with the carriage 64, it is shown to include a cylindrical side wall 74 from which a plurality of angled buttresses 76 radially outwardly extend terminating in a circular flange 78. The buttresses 76 and flange 78 are provided so as to dimensionally match the curved interior diameter of the base 22 in a stable fashion. A plurality of ledges 80 extend radially inward from the side wall 74.

Figure 7:
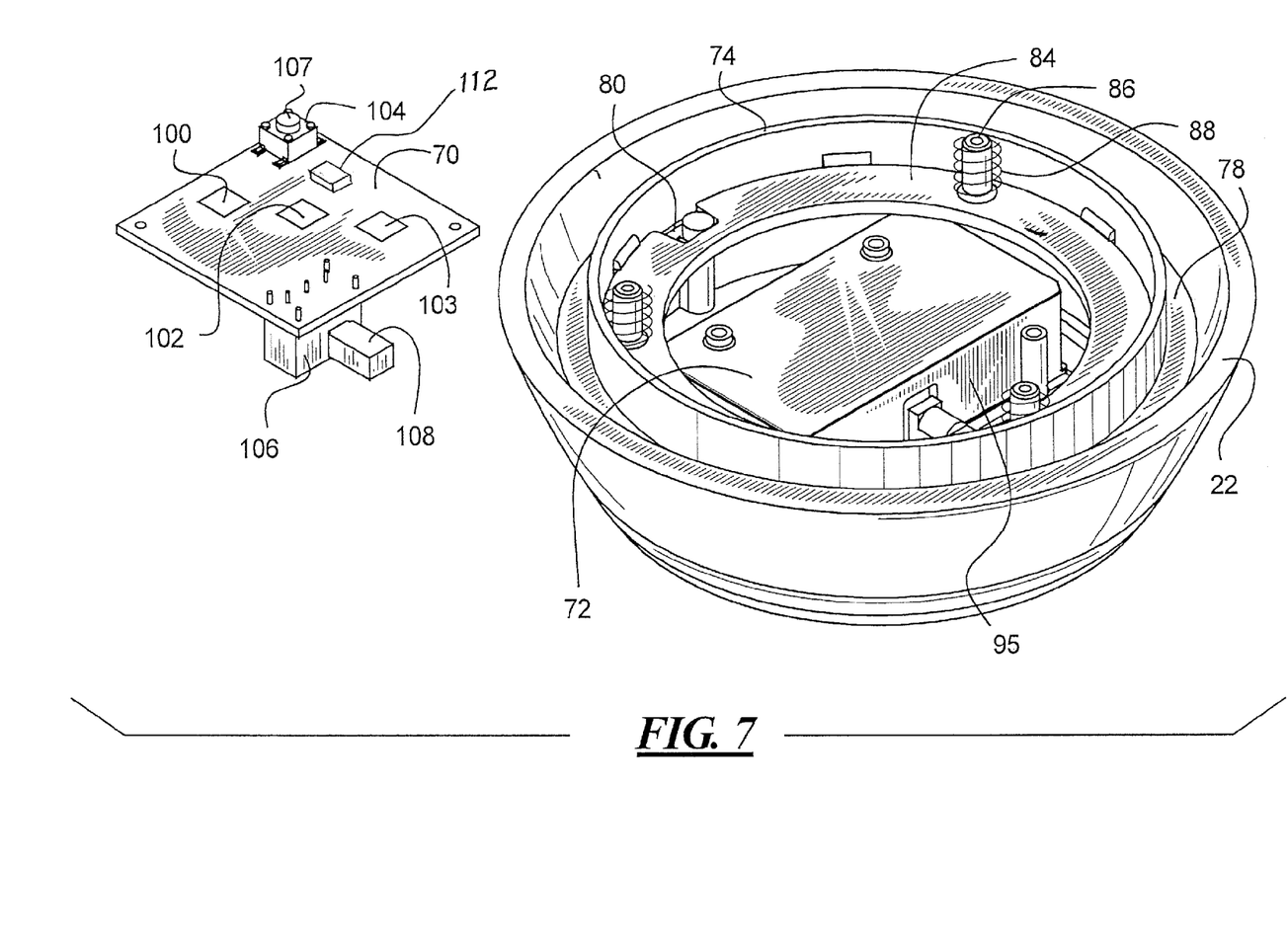
FIG. 7 is an enlarged isometric view of the vase with the circuit board exploded away.

Resting atop the plurality of ledges 80 is the lower platform 66. As best shown in FIG. 7, the lower platform 66 includes an annularly shaped substrate 84 from which upwardly extend a plurality of mounting legs 86. Setting atop the mounting legs 86 is the upper platform 68 which is also annular in shape. Springs 88 are mounted around each of the legs 86 so as to bias the two platforms away from each other. Extending upwardly from the upper platform 68 is a mounting bowl 90. As shown best in FIGS. 5 and 6, the mounting bowl 90 includes a top recess or keyhole 92 for receipt of the lock 56 of the upper vase. As will be described in further detail herein, the keyhole 92 is shaped complementarily to the shape of the lock 56. In order to conceal the electronics assembly 28, a curved, annular glamour plate 93 may be mounted over the mounting bowl 90.

Mounted below the lower platform 66 is the battery assembly 72. As shown best in FIG. 8, the battery assembly 72 includes a bottom plate 94 that mounts directly to the bottom wall 30 of the base 22. Four side walls 95 extend from a bottom plate 94 and form a compartment 96 for receipt of batteries (not shown). In addition, the bottom plate 94 is provided within a removable lid 98 to allow for user access into the battery compartment 96. The batteries may be conventional single-use alkaline batteries or rechargeable batteries. Alternatively, the battery assembly 72 may be replaced by a direct AC connection to wall outlet (not shown).

Resting atop the battery compartment 72 is the circuit board 70. The circuit board 70 includes suitable conductors, and circuitry for connection to the power source provided by the battery assembly 72. The circuit board further includes one or more light sources which may be in the form of one or more light emitting diodes (LEDs) 100. The circuit board 70 may further include a memory 102 for storage of one or more preprogrammed light shows, and a processor 103 for control of same. The circuit board 70 may further includes switches 104 and 106. The switch 104 may be a tact switch having a depressable button 107, while the switch 106 may be a key or slide switch have a slidable arm 108. In other embodiments not employing a light show, the light source may be directly connected to the power source without intervening electronics.

The circuit board 70 is sufficiently close to the upper platform 68, and more specifically the bottom surface 110, such that when the inner vase 26 is mounted and locked within the mounting bowl 90, the tact switch 104 can be activated simply by a downward sliding movement of the inner vase 26. In this embodiment, the inner vase pushes down against the mounting bowl 90 and upper platform 68. As the upper platform 68 is spring mounted to the lower platform 66, the springs 88 compress to allow this movement. Once the upper platform 68 engages the tact switch 104 and depresses the button 107, the device is turned on. The user can then release the inner vase 26 and the springs 88 return the upper platform 68, mounting bowl 90, and inner vase 26 to their elevated positions. The elements could be mounted relative to the lower platform 66 so as to allow for a certain degree of rotational deflection therebetween. Of course, the above-described activation mechanism of the switch 104 is not intended to limit the scope of this disclosure. Other activation methods, such as through direct engagement of the inner vase 26 and the switch 104, would be apparent to one of ordinary skill in the art without undue experimentation.

Figure 8:
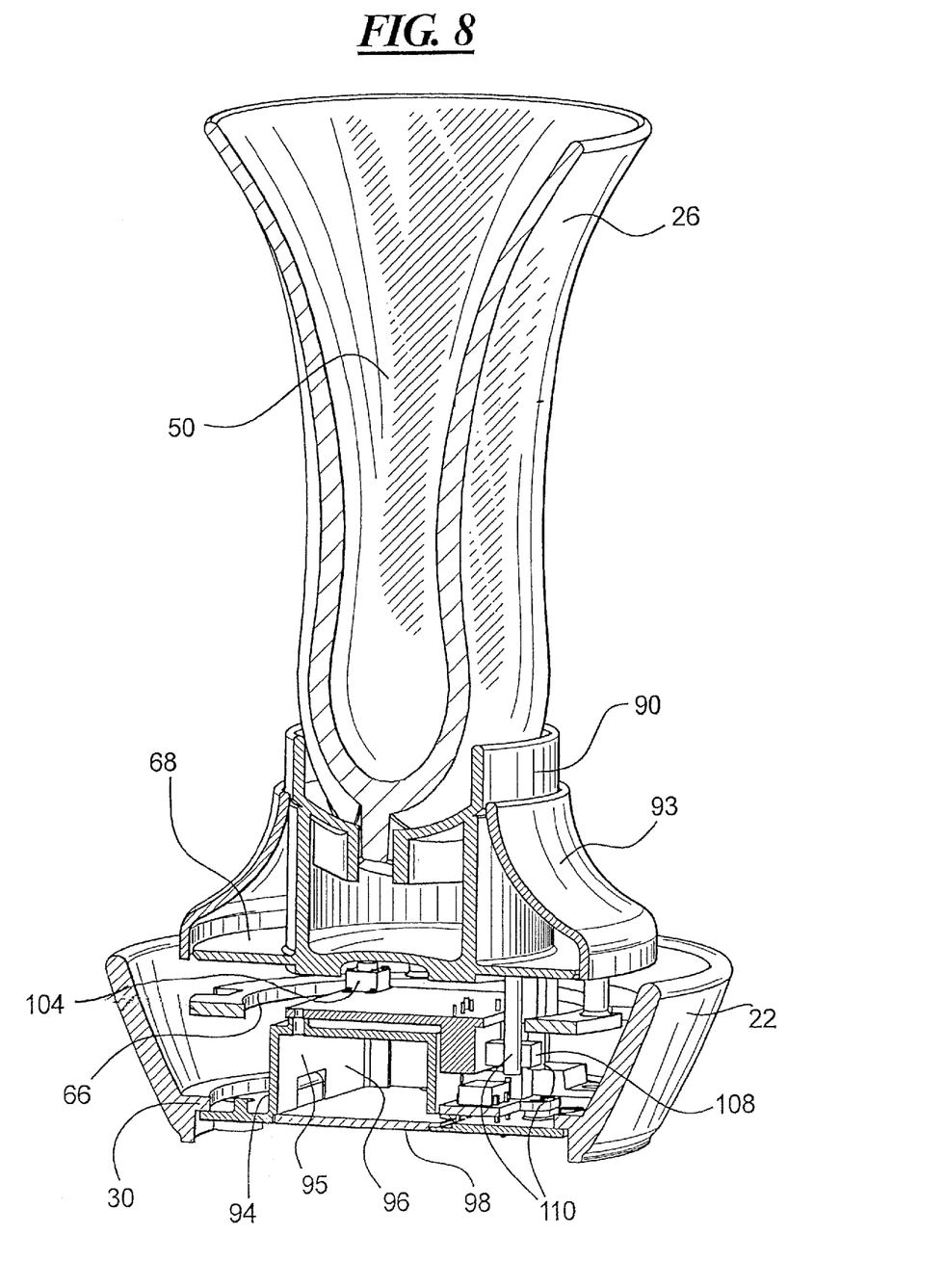
FIG. 8 is a perspective view, in cross-section, of the device of FIG. 1.

The key switch 106 is used to change the light show to be executed by the one or more LEDs. In order to do so, the upper platform 68 further includes two downwardly extending legs 110. As best shown in FIG. 8, the legs 110 laterally flank the slidable arm 108 of the key switch 106. Accordingly, when the user rotates the inner vase 26, the legs 110 are also rotated and the key switch arm 108 is slid into another position. This operation is aided by the lock 56 interfacing with the keyhole 92. Such a mating fit ensures rotation of the inner vase 26 and causes rotation of the upper platform 68. The lock 56 and its relationship with the upper platform 68 also requires an inner vase of the specific shape to be used thereby deterring use of other forms of unauthorized or unsafe refill vases.

Figure 11:
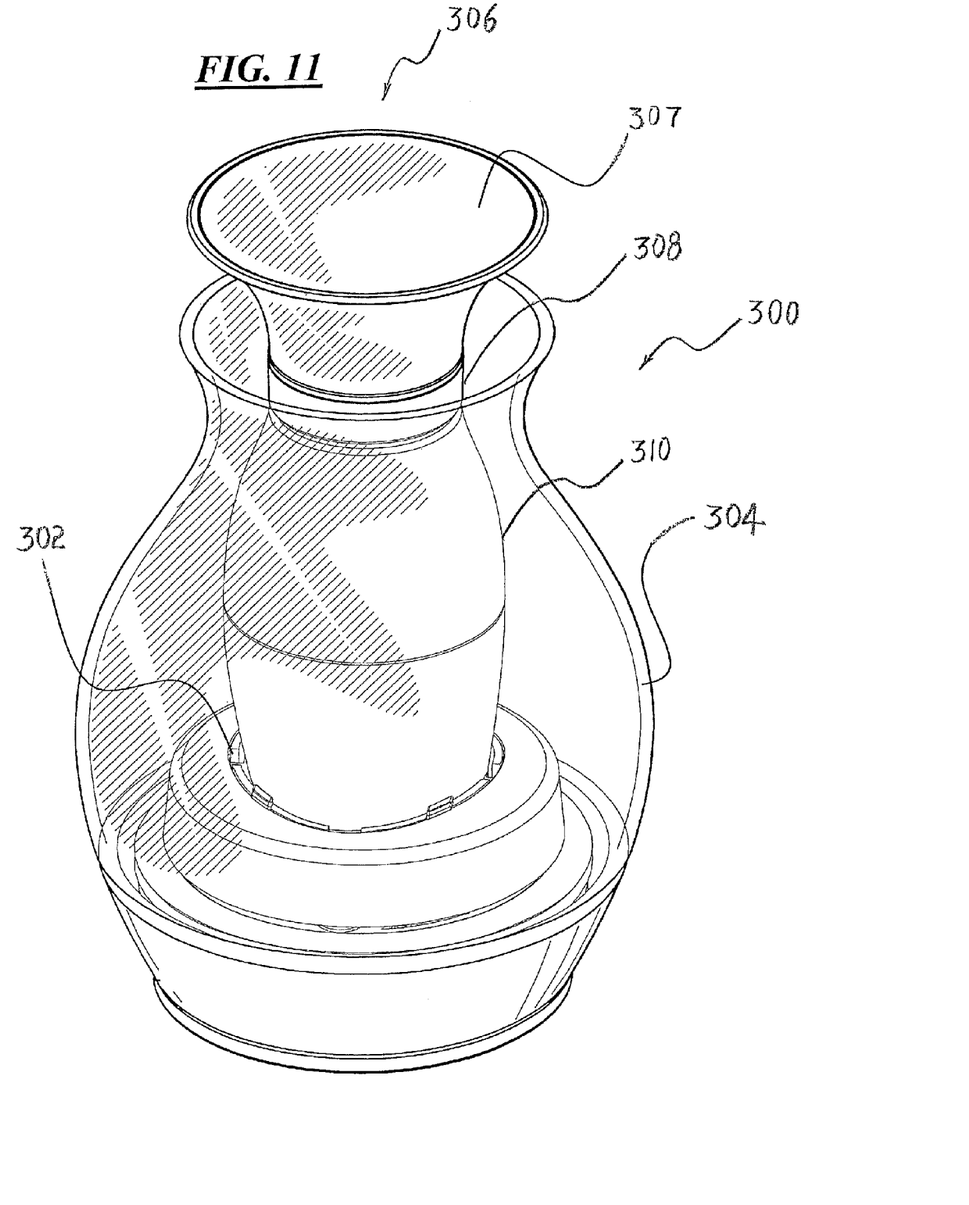
FIG. 11 is an isometric view of another alternative embodiment of a device constructed in accordance with the teachings of the disclosure.
Figure 12:
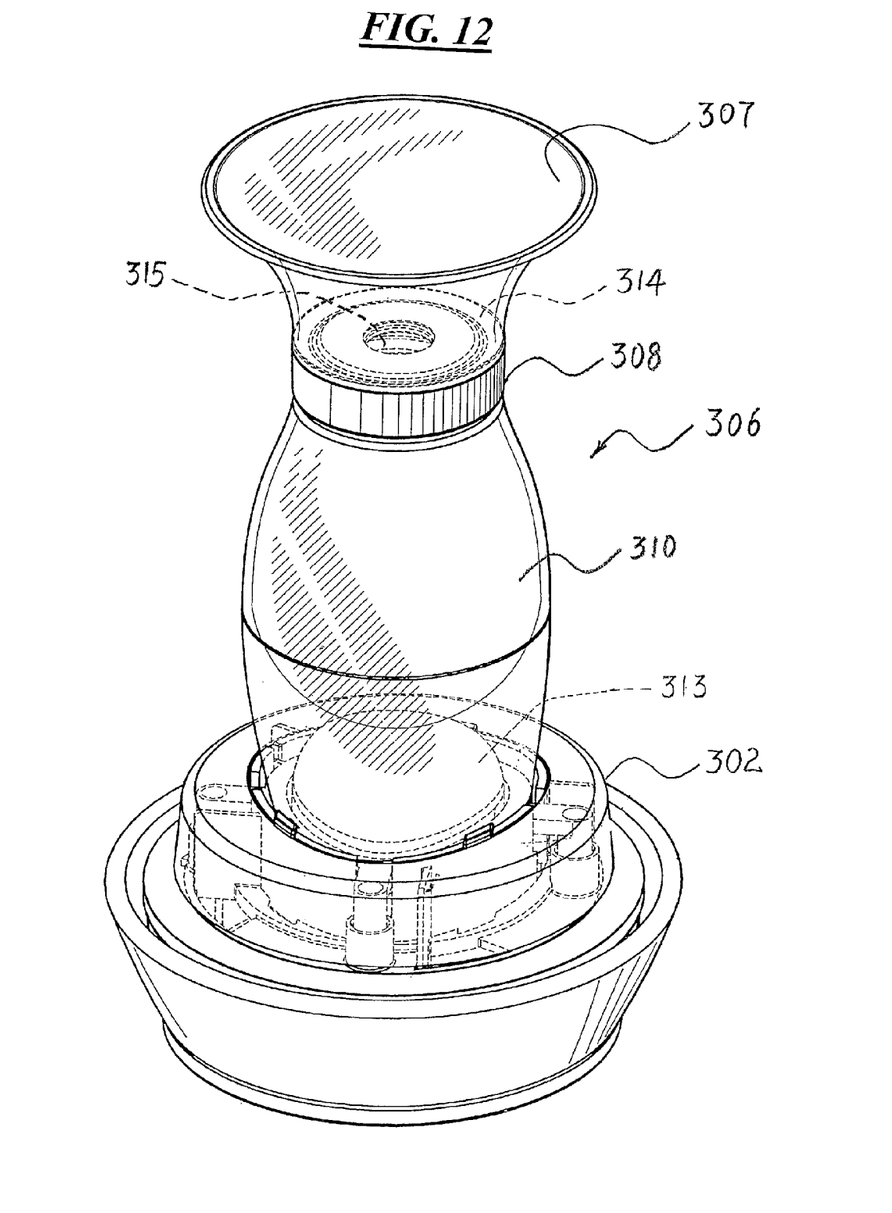
FIG. 12 is an isometric view of the device of FIG. 9 without the outer form, particularly illustrating the trilobe design of the locking mechanism.
Figure 13:
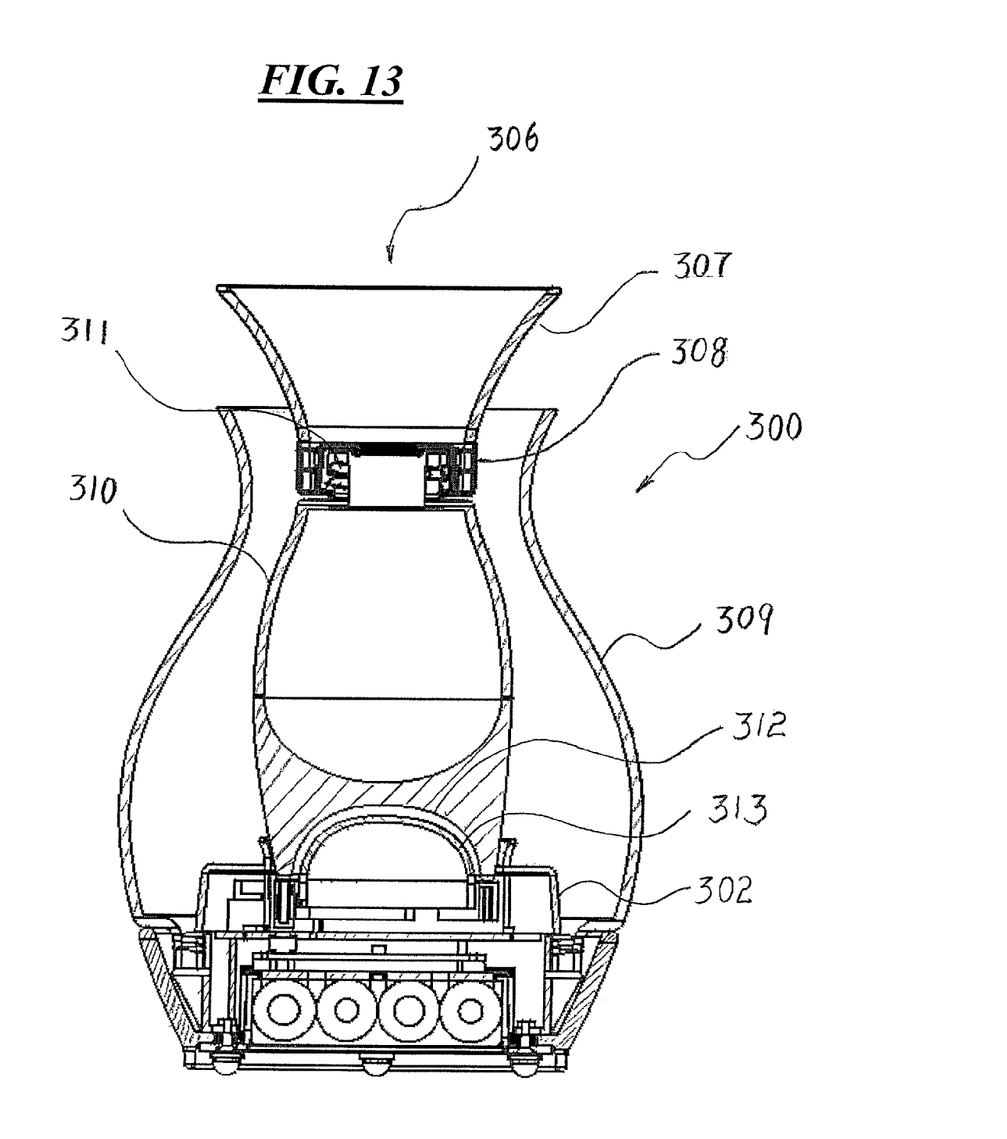
FIG. 13 is a side elevation view, in cross-section, of the device of FIG. 11.

Further, the inner vase 26 may be locked onto the base 22 through other locking mechanisms apparent to one of ordinary skill in the art. A non-limiting example of such alternative locking mechanisms is illustrated in FIGS. 11-13, in which the lock is provided on the base and the recess is provided on the inner vase. Specifically, the bottom of the reservoir 310 further includes a trilobe-shaped recess 312 that matably receives a trilobe-shaped lock 313 upwardly extending from the top center of the base 302. Of course, the shapes of the recess 312 and lock 313 in FIGS. 11-13 are for illustration purpose only and should not be construed as limiting the scope of this disclosure. Other shapes including, but not limited to, rectangular, square, triangle, star, polygon, oval, etc., would be apparent to one of ordinary skill in the art in view of this disclosure.

In other embodiments, different switching apparatus can be employed. For example, legs could extend through the bottom of the device and be mounted so as to be stationary relative to the surface on which the device is set, while the device as a whole pivots and/or reciprocates relative to the legs. In still further embodiments, the switches themselves may be external to the device so as to be easily accessible by the user. A remote control can also be used to control the device in a wireless capacity. It is to be understood, of course, that the position, type and operating mechanism of the switches are not to be construed as limiting the scope of this disclosure. One of ordinary skill in the art would be able to modify the switches described above in view of this disclosure without undue experimentation.

With respect to the actual light show that is executed by the device it could be any combination of the one or more LEDs in any conceivable sequence. For example, it could be a repeating cycle or pattern, a flickering show much like a candle, a static display of one color, a random execution of the lights, or the like. In addition, the devices can be used in combination by wireless network with their respective shows being synchronized.

An additional feature afforded by the form-within-a-form construction of one embodiment of the present disclosure is the unique air passageway provided between the inner and outer vases 26 and 24, respectively. As one of the features provided by the device 20 is that of chemical actives dispersion, such an air passageway can be used to augment the dispersal process through an air flow device 112, such as a fan, a heater, a piezo-electric device, or the like. In one embodiment, the air flow device 112 is provided in the disclosed dispenser to facilitate the air flow through the air passageway. The air flow device 112 may be mounted on a bottom portion of the inner or outer form or other suitable locations obvious to one of ordinary skill in the art. In the embodiment illustrated in FIG. 7, the air flow device 112 is a fan mounted on the base 22.

As the inner vase 26 is mounted relative to the outer vase 24 so as to define an interior annular channel 114, if a fan is so positioned and actuated, an air flow will be created through the annular channel 114 which ultimately exits relative to the top opening 42 of the outer vase 24. As the inner vase 26 is filled with the chemical active, such an air flow will cause the chemical active to be dispersed more quickly. This is particularly so if the aforementioned reeds or other forms of wicks are provided in the inner vase 26 to wick or otherwise draw the chemical active up and out of the device 20.

In addition to a fan, the air flow may be augmented through the use of a heater, a piezo-electric device, or the like. To meter or tailor the degree and rate of volatile active dissipation the air flow could be recycled multiple times past the active before being released to atmosphere. This recycling may be accomplished through the use of a labyrinthine pathway, valving or the like. It is also noteworthy that when an air flow device 112 is provided in the dispenser 20, the top opening 48 of the inner vase 26 may or may not extend beyond the top mouth 42 of the outer vase 24.

Figures 9, 10:
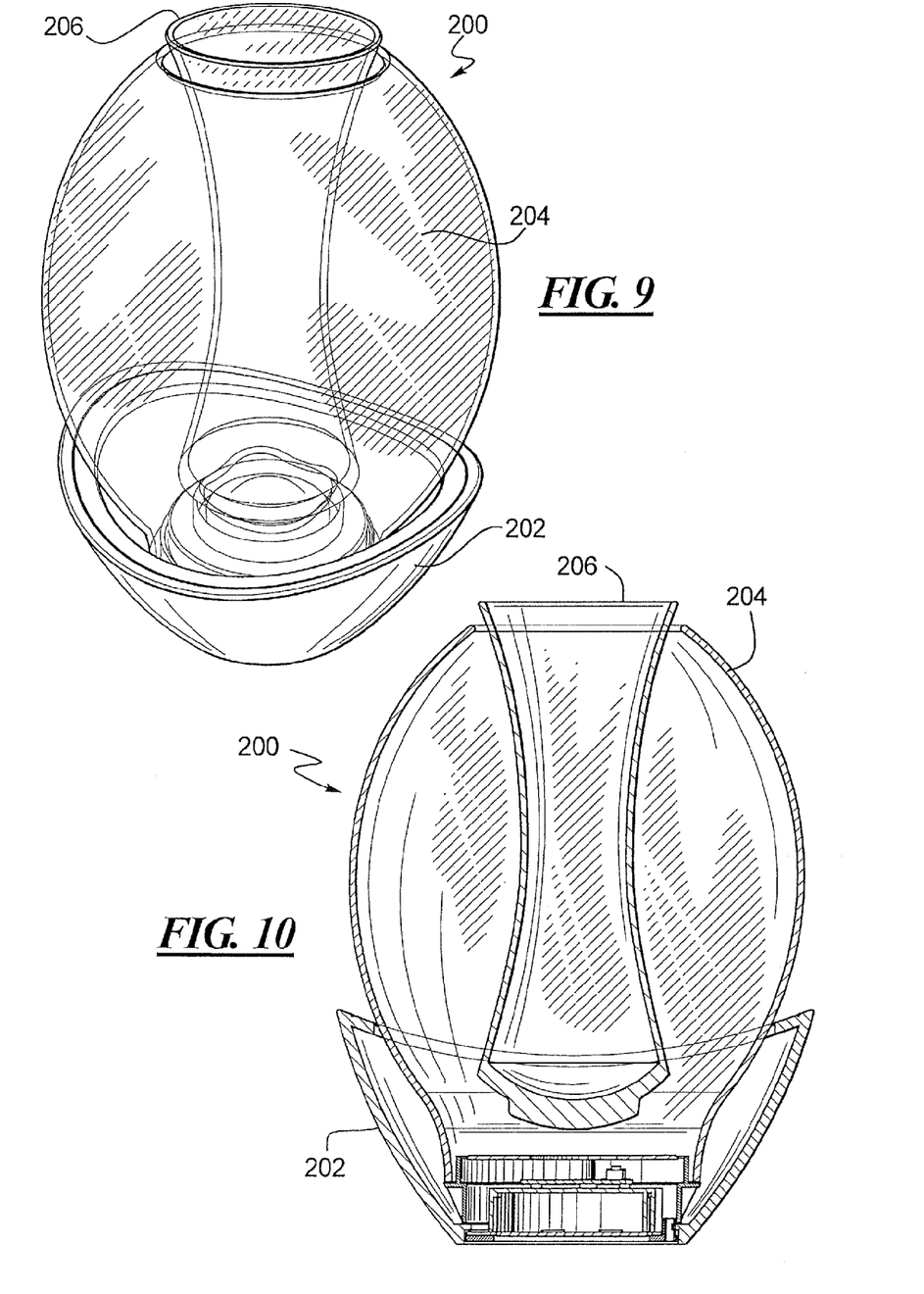
FIG. 9 is an isometric view of an alternative embodiment of a device constructed in accordance with the teachings of the disclosure.
FIG. 10 is a side elevation view, in cross-section, of the device of FIG. 9.

FIGS. 9 and 10 depict an alternative embodiment of the present disclosure. The device 200 includes substantially the same inner mechanics and electronics as the first embodiment, but with a differently shaped base 200, outer vase 204 and inner vase 206. More specifically, the base 202 is somewhat oval in horizontal cross-section, the outer vase 204 is somewhat spherical in shape, and the inner vase 206 is somewhat hour-glass in shape. Activation of the device and the light shows it executes are similar to the first embodiment.

From the foregoing, it can be seen that the pending disclosure sets forth a chemical actives dispersing device and light source. The device includes a plurality of glass, polymer or ceramic objects of an aesthetically pleasing design, but also which are able to refract and conduct light in an aesthetically pleasing fashion. In addition, the inner vase of the device is closed ended so as to provide a storage space for the chemical actives itself.

By mounting the inner vase relative to the outer vase in a specific fashion, unique air spaces are created which allow for the generation of air flow to aid in the dispersion of the chemical actives. Further, the electronics for driving the fan and the LED light source mounted within the electronic assembly of the device can be hidden by the use of an aesthetically pleasing but opaque base. A volume of volatile active may be provided within the inner vase with a plurality of reeds mounted therein to dissipate same.

Numerous modifications and variations of the present disclosure are possible in light of the above disclosure. It is therefore to be understood that, within the scope of the appended claims, the disclosure may be practiced otherwise than as specifically described herein. While only certain embodiments have been set forth, alternatives and modifications will be apparent from the above description to those skilled in the art. These and other alternatives are considered equivalents and within the spirit and scope of this disclosure and the appended claims.

What is claimed is:

1. A multi-sensory dispenser, comprising:
   an outer form defining an interior space;
   an inner form having an open top disposed above the interior space of the outer form and a closed bottom disposed within the interior space of the outer form;
   a volatile active disposed in one of the inner and outer forms;
   at least one reed having a bottom end in contact with the volatile active and a top end extending above the inner form and the outer form; and
   a light source disposed in a bottom portion of one of the inner and outer forms.

2. The dispenser of claim 1, wherein the outer form comprises a base that houses the light source.

3. The dispenser of claim 2, wherein the base is detachable.

4. The dispenser of claim 1, wherein the light source comprises at least one LED.

5. The dispenser of claim 1, further comprising a circuit board in operative association with the light source.

6. The dispenser of claim 5, wherein the circuit board comprises a memory for storing at least one preprogrammed light show and a processor that controls the at least one LED to display the light show.

7. The dispenser of claim 5, wherein the circuit board comprises a switch that is activated by a sliding movement of the inner form toward the bottom of the outer form.

8. The dispenser of claim 5, wherein the circuit board comprises a switch that is activated by a rotational movement of the inner form.

9. A multi-sensory dispenser, comprising:
    a base having a top recess;
    an inner form having an open top and a closed bottom, the bottom comprising a lock shaped to be matably received in the top recess of the base;
    a volatile active disposed in the inner form; and
    a light source disposed in the base.

10. The dispenser of claim 9, further comprising an outer form upwardly extending from the base around the inner form.

11. The dispenser of claim 9, wherein the light source comprises at least one LED.

12. The dispenser of claim 9, further comprising a circuit board in operative association with the light source.

13. The dispenser of claim 12, wherein the circuit board comprises a memory for storing at least one preprogrammed light show and a processor that controls the at least one LED to display the light show.

14. The dispenser of claim 12, wherein the circuit board comprises a switch that is activated by a sliding movement of the inner form toward the base.

15. The dispenser of claim 12, wherein the circuit board comprises a switch that is activated by a rotational movement of the inner form.

16. A multi-sensory dispenser, comprising:
    an outer form;
    an inner form, the inner and outer forms defining an air passageway therebetween;
    a volatile active disposed in one of the inner and outer forms;
    a light source disposed in a bottom portion of one of the inner and outer forms, the light source comprising at least one LED;
    a circuit board in operative association with the light source, the circuit board comprising a memory for storing at least one preprogrammed light show and a processor that controls the at least one LED to display the light show; and
    an air flow enhancer mounted on a bottom portion of one of the inner and outer forms to facilitate air flow through the air passageway.

* * * * *